(12) United States Patent
Wei et al.

(10) Patent No.: US 9,618,523 B2
(45) Date of Patent: Apr. 11, 2017

(54) METHODS AND REAGENTS FOR DETERMINING ISOMERIC ANALYTES

(71) Applicants: Tie Q. Wei, Wilmington, DE (US); Izak Bahar, Hockessin, DE (US)

(72) Inventors: Tie Q. Wei, Wilmington, DE (US); Izak Bahar, Hockessin, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 138 days.

(21) Appl. No.: 13/780,305

(22) Filed: Feb. 28, 2013

(65) Prior Publication Data

US 2014/0242615 A1 Aug. 28, 2014

(51) Int. Cl.
*G01N 33/82* (2006.01)
*G01N 33/53* (2006.01)

(52) U.S. Cl.
CPC ......... *G01N 33/82* (2013.01); *G01N 33/5308* (2013.01)

(58) Field of Classification Search
None
See application file for complete search history.

(56) References Cited

U.S. PATENT DOCUMENTS

| | | | |
|---|---|---|---|
| 4,456,553 A | | 6/1984 | Oshida et al. |
| 4,722,889 A | * | 2/1988 | Lee et al. ............... 435/7.94 |
| 4,816,417 A | | 3/1989 | DeLuca et al. |
| 5,026,653 A | * | 6/1991 | Lee et al. ............... 436/518 |
| 5,075,465 A | | 12/1991 | Nakagawa et al. |
| 5,093,519 A | | 3/1992 | Bouillon et al. |
| 5,340,716 A | * | 8/1994 | Ullman et al. ............. 435/6.12 |
| 5,589,401 A | * | 12/1996 | Hansen et al. ............. 436/525 |
| 5,786,347 A | | 7/1998 | Hesse et al. |
| 5,821,020 A | | 10/1998 | Hollis |
| 5,981,779 A | | 11/1999 | Holick et al. |
| 6,291,693 B1 | | 9/2001 | Holick et al. |
| 6,787,660 B1 | | 9/2004 | Armbruster et al. |
| 6,929,797 B2 | | 8/2005 | Mazess et al. |
| 7,087,395 B1 | | 8/2006 | Garrity et al. |
| 7,482,162 B2 | | 1/2009 | Lauric et al. |
| 7,635,571 B2 | | 12/2009 | Ullman et al. |
| 7,745,226 B2 | | 6/2010 | Clarke et al. |
| 8,173,442 B2 | | 5/2012 | Holmquist et al. |
| 8,785,603 B2 | | 7/2014 | Sahakian et al. |
| 2004/0132104 A1 | | 7/2004 | Sackrison et al. |
| 2005/0014211 A1 | | 1/2005 | Armbruster et al. |
| 2008/0317764 A1 | | 12/2008 | Huber et al. |
| 2009/0137056 A1 | | 5/2009 | Holmquist et al. |
| 2009/0142358 A1 | | 6/2009 | Zhu |
| 2010/0120169 A1 | * | 5/2010 | Dodds et al. ............. 436/500 |
| 2011/0318754 A1 | * | 12/2011 | Wei ............... 435/7.9 |
| 2012/0190046 A1 | | 7/2012 | Datta et al. |
| 2012/0190121 A1 | | 7/2012 | Holmquist et al. |

FOREIGN PATENT DOCUMENTS

| | | | | |
|---|---|---|---|---|
| EP | 0583945 A2 | | 2/1994 | |
| GB | WO 9011525 A1 | * | 10/1990 | ........... G01N 21/553 |
| WO | WO 9826644 A2 | * | 6/1998 | |
| WO | WO 0050860 A1 | * | 8/2000 | ............... G01J 3/30 |
| WO | 02057797 A2 | | 7/2002 | |
| WO | 2004063704 A2 | | 7/2004 | |
| WO | 2005040222 A1 | | 5/2005 | |
| WO | 2007039193 A1 | | 4/2007 | |
| WO | 2007039194 A1 | | 4/2007 | |
| WO | 2007140962 A2 | | 12/2007 | |
| WO | WO 2011122948 A1 | * | 10/2011 | ............. G01N 33/82 |

OTHER PUBLICATIONS

Singh et al., C-3 epimers can account for a significant proportion of total circulating 25-hydroxyvitamin D in infants, complicating accurate measurement and interpretation of vitamin D status, The Journal of Clinical Endocrinology & Metabolism 91(8), 3055-3061, 2006.*
Bioventix, Safety Datasheet, 2010, 2 pages retrieved from http://www.bioventix.com/index_htm_files/MSDS-VitD3.5H10.pdf on Nov. 6, 2013.*
ADVIA Centaur Vitamin D Total Assay Specifications, 2011, 2 pages, retrieved from http://www.medical.siemens.com/siemens/en_GLOBAL/gg_diag_FBAs/files/products_disease_states/bone_metabolism/110781-GC1_Vitamin_D_on_ADVIA_Centaur_SS_Final.pdf on Nov. 6, 2013.*
Ullman et al., Luminescent oxygen channeling assay (LOCI): sensitive, broadly applicable homogeneous immunoassay method, Clin Chem. Sep. 1996;42(9):1518-26.*
J. Freeman, et al., Development of the ADVIA Centaur(R) Systems Vitamin D Total Assay, Clinical Chemistry, vol. 56, No. 6, Supplement, 2010, p. A153-A154.
Elizabeth A. Yetley, et al., NHANES Monitoring of Serum 25-Hydroxyvitamin D: A Roundtable Summary, the Journal of Nutrition, Supplement, 2010, p. 2030S-2045S.
Graham D. Carter, 25-Hydroxyvitamin D: A Difficult Analyte, Clinical Chemistry, 58:3, 2012, p. 486-488.
International Search Report and Written Opinion of International Application No. PCT/US2014/018620 dated May 21, 2014.
Moon et al., "Comparison of four current 25-hydroxyvitamin D assays", 2012, Clinical Biochemistry vol. 45, pp. 326-330.
European Search Report and Search Opinion of European Application No. 14756548 dated Oct. 27, 2016.

* cited by examiner

*Primary Examiner* — Andrea S Grossman
(74) *Attorney, Agent, or Firm* — Theodore J. Leitereg

(57) ABSTRACT

Methods include determining in a sample an amount of a first isomeric analyte and a second isomeric analyte. A first measurement value and a second measurement value are determined. The first measurement value represents a total amount of the first isomeric analyte and the second isomeric analyte. The second measurement value represents an amount of the second isomeric analyte only. The second measurement value is subtracted from the first measurement value to obtain a resulting value and the resulting value is equated to an amount of the first isomeric analyte in the sample.

4 Claims, 3 Drawing Sheets

METHODS AND REAGENTS FOR DETERMINING ISOMERIC ANALYTES

BACKGROUND

This invention relates to compositions, methods and kits for determining the presence and/or amount of each of two or more isomeric analytes in a sample suspected of containing the isomeric analytes.

Many small molecule compounds or haptens such as, for example, drugs and vitamins, exist in isomeric forms, of which only one form is active. In order to obtain an accurate measurement of the active form of an analyte, the presence of the non-active isomer of the analyte must be addressed. Measurements of both isomeric forms of an analyte, that is, active and non-active forms, can lead to inaccuracies that may be detrimental to an individual depending on the function of the active form of the analyte. Accurately assessing the level of each of a pair of isomeric analytes in biological samples is important especially where only one of the isomers is active and measurements that include the amount of the non-active isomer distort the level of the analyte in a sample. For example, measuring vitamin D levels in biological samples is important since vitamin D deficiency is related to a number of disorders in mammals. In infants, for example, vitamin D measurements that include amounts of 3-epi isomers can lead to inaccurate assessment of vitamin D levels in the infant, which in turn can lead to a lack of proper supplementation. It is important to measure the active form of vitamin D so that an infant can receive proper vitamin D therapy, if necessary.

The term "vitamin D" refers to a group of fat-soluble secosteroids. In humans, vitamin D is unique because it can be ingested as cholecalciferol (vitamin $D_3$) or ergocalciferol (vitamin $D_2$) and because the body can also synthesize it (from cholesterol) when sun exposure is adequate. Because of this latter property, vitamin D is considered by some to be a non-essential dietary vitamin although most consider it an essential nutrient. Vitamin D has an important physiological role in the positive regulation of calcium ion homeostasis. Vitamin $D_3$ is the form of the vitamin synthesized by animals. It is also a common supplement added to milk products and certain food products as is vitamin $D_2$.

Both dietary and intrinsically synthesized vitamin $D_3$ must undergo metabolic activation to generate bioactive metabolites. In humans, the initial step of vitamin $D_3$ activation occurs primarily in the liver and involves hydroxylation to form the intermediate metabolite 25-hydroxycholecalciferol (also referred to as calcidiol, calcifediol, 25-hydroxycholecalciferol, or 25-hydroxyvitamin $D_3$. Calcidiol is the major form of Vitamin $D_3$ in the circulatory system. Vitamin $D_2$ also undergoes similar metabolic activation to 25-hydroxyvitamin $D_2$. Collectively these compounds are called 25-hydroxyvitamin D (abbreviated 25(OH)D) and they are the major metabolites that are measured in serum to determine vitamin D status; 25(OH)D and its epimers are both pre-hormones that need to be converted into 1,25(OH)D to exert biological functions. The comparison of bioactivity of 1,25(OH)D versus that of 3-epi-1,25(OH)D is complex.

The vitamin D compounds 25-hydroxyvitamin $D_3$ and 25-hydroxyvitamin $D_2$ are epimeric at the 3-position with the epimers being designated 25-hydroxyvitamin $D_3$ and 3-epi-25-hydroxyvitamin $D_3$ and 25-hydroxyvitamin $D_2$ and 3-epi-25-hydroxyvitamin $D_2$, respectively. Only one of the epimers of each of these epimeric compounds, namely, 25-hydroxyvitamin $D_3$ and 25-hydroxyvitamin $D_2$, respectively, are active. The structures for the epimers of 25-hydroxyvitamin $D_3$ and 25-hydroxyvitamin $D_2$ are set forth in FIG. 1.

There is a need for reagents and methods for accurate and sensitive determinations of concentrations of isomeric analytes in samples suspected of containing such analytes. For example, there is a need for reagents and methods for accurate and sensitive determinations of concentrations of epimeric forms of vitamin D.

SUMMARY

Some examples in accordance with the principles described herein are directed to methods of determining in a sample an amount of a first isomeric analyte and a second isomeric analyte. In the method a first measurement value and a second measurement value are determined. For determination of the first measurement value, a total amount of the first isomeric analyte and the second isomeric analyte is measured by conducting an assay on a portion of the sample using a first antibody that exhibits sufficient assay binding affinity for each of the first isomeric analyte and the second isomeric analyte. For determination of the second measurement value, an amount of the second isomeric analyte is measured by conducting the assay on a portion of the sample using the first antibody, wherein a second antibody that binds to the first isomeric analyte but exhibits insufficient assay binding affinity for the first isomeric analyte and substantially no assay binding affinity for the second isomeric analyte is employed in excess to block binding of the first isomeric analyte to the first antibody. The second measurement value is equated to an amount of the second isomeric analyte in the sample. The second measurement value is subtracted from the first measurement value to obtain a resulting value and the resulting value is equated to an amount of the first isomeric analyte in the sample.

Some examples in accordance with the principles described herein are directed to methods of determining in a sample an amount of a first isomeric analyte and a second isomeric analyte. In the method a first measurement value and a second measurement value are determined. For determination of the first measurement value, a total amount of the first isomeric analyte and the second isomeric analyte is measured by conducting an assay on a portion of the sample using a first antibody having a binding affinity for each of the first isomeric analyte and the second isomeric analyte of at least about $10^7$ liters/mole. For determination of the second measurement value, an amount of the second isomeric analyte is measured by conducting the assay on a portion of the sample using the first antibody to obtain a second measurement value, wherein a second antibody that has a binding affinity for the first isomeric analyte of about $10^6$ to about $10^{12}$ liters/mole and a binding affinity for the second isomeric analyte of less than about $10^4$ liters/mole is employed in excess to block binding of the first isomeric analyte to the first antibody. The second measurement value is equated to an amount of the second isomeric analyte in the sample and the second measurement value is subtracted from the first measurement value to obtain a resulting value, which is equated to an amount of the first isomeric analyte in the sample.

DETAILED DESCRIPTION OF SPECIFIC EMBODIMENTS

General Discussion

Figure 1:
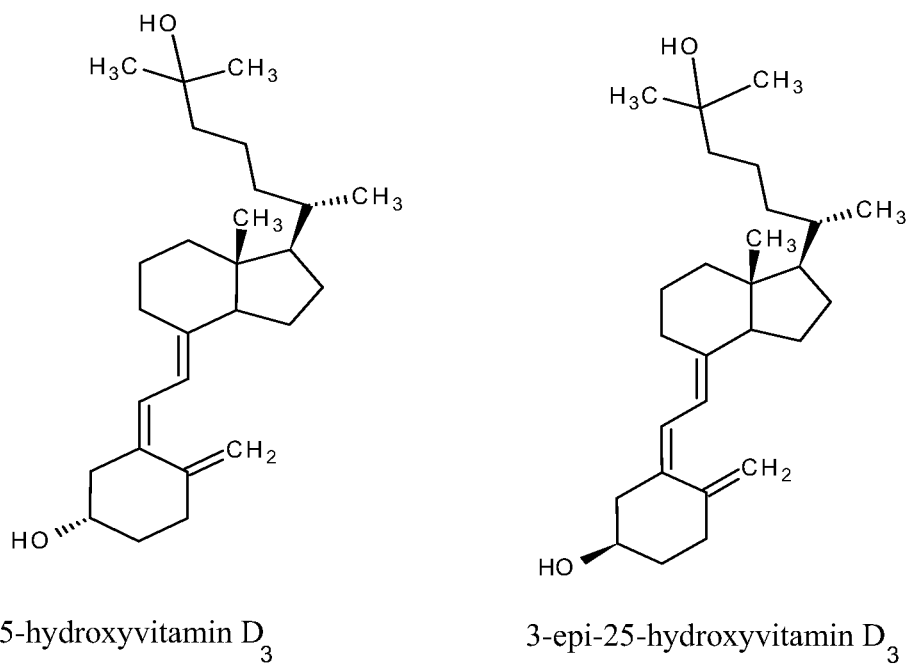
FIG. 1 is a depiction of the chemical formulas for the epimeric forms of 25-hydroxyvitamin $D_3$ and 25-hydroxyvitamin $D_2$.
Figure 1:
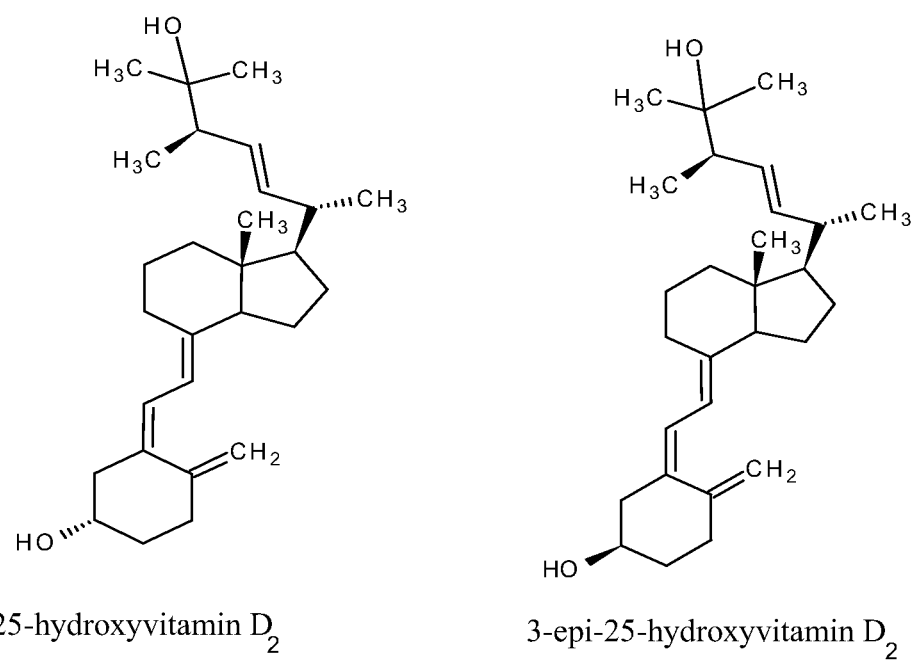

Methods in accordance with the principles described herein minimize cross-reactivity of, and measure an amount of, one of two isomers of an analyte where one of the isomers or its metabolic product is potent and the other or its metabolic product is not. The term "potent" refers to the degree of an activity of an analyte with respect to a particular function, which may be, for example, a biological function such as, e.g., bone metabolism. For example, biological activity of a substance relates to the ability of the substance to enhance or suppress a biological function such as, for example, maintaining appropriate levels of minerals and salts in a subject, cellular function. Vitamin D, by way of illustration and not limitation, maintains appropriate levels of calcium and phosphate in a subject, which relate to calcium homeostasis and bone metabolism.

Methods include determining in a sample an amount of a first isomeric analyte and a second isomeric analyte. A first measurement value and a second measurement value are determined. The first measurement value represents a total amount of the first isomeric analyte and the second isomeric analyte. The second measurement value represents an amount of the second isomeric analyte only. The second measurement value is subtracted from the first measurement value to obtain a resulting value and the resulting value is equated to an amount of the first isomeric analyte in the sample.

In methods in accordance with the principles described herein, at least two portions of a sample to be analyzed are utilized. An assay is carried out on a first portion of the sample suspected of containing at least two isomeric forms of an analyte using an antibody (first antibody) that binds to both isomeric forms of the analyte. The first antibody exhibits sufficient assay binding affinity for each of the first isomeric analyte and the second isomeric analyte.

The phrase "assay binding affinity" refers to the strength with which an antibody binds to a corresponding analyte to produce a complex of antibody bound to analyte.

The phrase "sufficient assay binding affinity" means that the binding affinity of an antibody for an analyte is that which produces a detectable complex in an amount sufficient to obtain an assay signal that results in an accurate and sensitive determination of the analyte. The binding affinity of the first antibody is strong enough to form detectable complexes of the first antibody and the each of the first isomeric analyte and the second isomeric analyte where the detectable complexes accurately represent the amount of the first isomeric analyte and the second isomeric analyte in the sample once the assay system and instrument have been subjected to suitable calibration and any correction factors for antibody recognition of one or both of the isomeric analytes have been applied. This assay on the first portion of the sample measures the amount or concentration of both isomeric forms of an analyte in a sample.

The same assay is conducted on a second portion of the same sample using both the first antibody that binds to both isomeric forms of the analyte and a second antibody that binds to one of the isomeric forms (first isomeric form) but exhibits substantially no binding affinity for the other isomeric form (second isomeric form) leaving the second isomeric form free for detection by the first antibody in the assay conducted on the second portion. The second antibody that binds to the first isomeric form but not to the second isomeric form exhibits insufficient assay binding affinity for the first isomeric analyte. In some examples, the second antibody that binds to one of the isomeric forms but not to the other isomeric form binds to the active isomeric form but not to the non-active isomeric form. This assay on the second portion of the sample measures the concentration of only one of the isomeric forms of the analyte, namely, the second isomeric analyte in the above description. The signal values obtained may be used to determine the total analyte concentration and the concentration of each of the two isomeric forms of the analyte.

The phrase "insufficient assay binding affinity" means that the binding affinity of the second antibody for an isomeric analyte is less than the binding affinity of the first antibody for the isomeric analyte. In some examples, the phrase "insufficient assay binding affinity" means that the binding affinity of the second antibody for an isomeric analyte is not great enough to form detectable complexes between the second antibody and the first isomeric analyte and thus any detectable complexes do not accurately represent the amount of the first isomeric analyte. The second antibody, when used in excess, exhibits sufficient binding affinity for the first isomeric analyte to block binding of the first antibody to the first isomeric analyte in the assay on the second portion of the sample. The binding affinity of the second antibody for the first isomeric form of the analyte is too low to generate complexes of second antibody and first isomeric analyte so that sufficient signal for accurate detection of the first isomeric analyte is produced in the assay employed.

The phrase "exhibits substantially no binding affinity" for the second isomeric form means that substantially no detectable complexes are formed between the second antibody and the second isomeric form of the analyte.

It should be noted that, if the result from the assay on the second portion of the sample is substantially equivalent to zero, then the result obtained from the assay on the first portion of the sample represents the concentration of only one of the two isomeric forms of the analyte since that the other isomeric form of the analyte is not detected in the assay on the second portion of the sample. In such a circumstance, it would not be necessary to conduct assays on two portions of the sample in question since the results from the methods in accordance with the principles described herein indicate that only one of the isomeric forms of the analyte is contributing to signal obtained in the assay on the first portion of the sample. On the other hand, if the result from the assay on the second portion of the sample is not substantially equivalent to zero, then the result obtained from the assay on the first portion of the sample represents the concentration of both of the two isomeric forms of the analyte since the other isomeric form of the analyte is detected in the assay on the second portion of the sample. In such a circumstance, it would be necessary to conduct assays on two portions of the sample in question since the results from the methods in accordance with the principles described herein indicate that both of the isomeric forms of the analyte are contributing to signal obtained in the assay on the first portion of the sample.

Preparation of Antibodies

Examples of methods of preparing antibodies in accordance with the principles described herein are described by way of illustration and not limitation. At least two different antibodies are required, which have the properties in accordance with the principles described herein. One antibody exhibits sufficient assay binding affinity for both the first isomeric analyte and the second isomeric analyte. The other antibody binds to the first isomeric analyte but exhibits insufficient assay binding affinity for the first isomeric analyte and exhibits substantially no assay binding affinity for the second isomeric analyte.

In some examples in accordance with the principles described herein, sufficient assay binding affinity is at least about $10^7$ liters/mole, or at least about $10^8$ liters/mole, or at least about $10^9$ liters/mole, or at least about $10^{10}$ liters/mole, or at least about $10^{11}$ liters/mole, or at least about $10^{12}$ liters/mole, or at least about $10^{13}$ liters/mole, or at least about $10^{14}$ liters/mole, for example, and the amount of detectable complex is sufficient to obtain an assay signal that results in an accurate and sensitive determination of the analyte. In some examples in accordance with the principles described herein, sufficient assay binding affinity is about $10^7$ to about $10^{14}$ liters/mole, or about $10^7$ to about $10^{11}$ liters/mole, or about $10^7$ to about $10^{12}$ liters/mole, or about $10^8$ to about $10^{14}$ liters/mole, or about $10^8$ to about $10^{11}$ liters/mole, or about $10^8$ to about $10^{12}$ liters/mole, for example, In some examples, insufficient assay binding affinity means that the binding affinity of the second antibody for a first isomeric analyte is less than the binding affinity of the first antibody for the first isomeric analyte. In some examples, depending on the binding affinity of the first antibody for the first isomeric analyte, the binding affinity of the second antibody for a first isomeric analyte is less than the binding affinity of the first antibody for the first isomeric analyte by a factor, for example, of about 10, or about $10^2$, or about $10^3$, or about $10^4$, or about $10^5$. For example, if the binding affinity of the first antibody for the first isomeric analyte is about $10^9$ liters/mole, the binding affinity of the second antibody may be less that about $10^7$ liters/mole, or less than about $10^6$ liters/mole. In some examples in accordance with the principles described herein, insufficient assay binding affinity means that the binding affinity of an antibody for an analyte is about $10^6$ to about $10^8$ liters/mole, or about $10^6$ to about $10^7$ liters/mole, for example, depending on the nature of the antibody and the nature of the analyte.

In some examples, substantially no binding affinity means that an antibody has a binding affinity for an isomeric analyte of less than about $10^4$ liters/mole, or less than about $10^3$ liters/mole, or less than about $10^2$ liters/mole, or less than about 10 liters/mole, for example.

In the above discussion, binding affinity is specific binding affinity, which involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules.

The antibody may be monoclonal or polyclonal. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Monoclonal antibodies can be prepared by techniques that are well known in the art such as preparing continuous hybrid cell lines and collecting the secreted protein (somatic cell hybridization techniques). Monoclonal antibodies may be produced according to the standard techniques of Köhler and Milstein, *Nature* 265:495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981).

In another approach for the preparation of antibodies, the sequence coding for antibody binding sites can be excised from the chromosome DNA and inserted into a cloning vector, which can be expressed in bacteria to produce recombinant proteins having the corresponding antibody binding sites. This approach involves cloning and expressing nucleotide sequences or mutagenized versions thereof coding at least for the amino acid sequences required for specific binding of natural antibodies.

In one approach for the production of monoclonal antibodies, a first step includes immunization of an antibody-producing animal such as a mouse, a rat, a goat, a sheep, or a cow with the antigen, for example, with an immunogen. Immunization can be performed with or without an adjuvant such as complete Freund's adjuvant or other adjuvants such as monophosphoryl lipid A and synthetic trehalose dicorynomycolate adjuvant. A next step includes isolating spleen cells from the antibody-producing animal and fusing the antibody-producing spleen cells with an appropriate fusion partner, typically a myeloma cell, such as by the use of polyethylene glycol or other techniques. Typically, the myeloma cells used are those that grow normally in hypoxanthine-thymidine (HT) medium but cannot grow in hypoxanthine-aminopterin-thymidine (HAT) medium, used for selection of the fused cells. A next step includes selection of the fused cells, typically by selection in HAT medium. A next step includes screening the cloned hybrids for appropriate antibody production using immunoassays such as enzyme-linked immunosorbent assay (ELISA) or other immunoassays appropriate for screening.

The term "immunogenic carrier" means a group or moiety which, when conjugated to a hapten and injected into a mammal or otherwise employed as an immunogen, induces an immune response and elicits production of antibodies that bind to the hapten. Immunogenic carriers are also sometimes referred to as antigenic carriers. In some examples in accordance with the principles described herein, immunogens comprising immunogenic carriers, including poly(amino acid) and non-poly(amino acid) immunogenic carriers, linked to an immunosuppressant compound at a particular position are synthesized and used to prepare antibodies. Haptens are compounds capable of binding specifically to corresponding antibodies, but do not themselves act as immunogens (or antigens) for preparation of the antibodies. Consequently, a hapten is linked to an immunogenic carrier, which is employed to raise antibodies.

The molecular weight range (in Daltons) for poly(amino acids) that are immunogenic carriers is about 5,000 to about 10,000,000, or about 20,000 to about 600,000, or about 25,000 to about 250,000 molecular weight, for example. Poly(amino acid) immunogenic carriers include proteins such as, for example, albumins, serum proteins, e.g., globulins, ocular lens proteins and lipoproteins. Illustrative proteins include, but are not limited to, bovine serum albumin (BSA), keyhole limpet hemocyanin (KLH), egg ovalbumin, and bovine gamma-globulin (BGG), for example. Non-poly (amino acid) immunogenic carriers include polysaccharides, nucleic acids and particles (biologic and synthetic materials). A wide variety of immunogenic carriers are disclosed in Davalian, et al., U.S. Pat. No. 5,089,390, column 4, line 57 to column 5, line 5, which is incorporated herein by reference.

As mentioned above, the immunogenic carrier may be a polysaccharide, which is a high molecular weight polymer of monosaccharides that may be prepared naturally or synthetically and usually involves repeated condensations of monosaccharides. Examples of polysaccharides are starches, glycogen, cellulose, carbohydrate gums, such as gum arabic, agar, and so forth. The polysaccharide can also contain poly(amino acid) residues and/or lipid residues.

As mentioned above, in some examples in accordance with the principles described herein, the immunogenic carrier may be linked to an analyte analog at a predetermined position on the analyte by means of a linking group. In some examples, the linking group may comprise about 2 to about 50 atoms, or 4 to about 30 atoms, not counting hydrogen and may comprise a chain of from 2 to about 30 atoms, or 3 to about 20 atoms, each independently selected from the group normally consisting of carbon, oxygen, sulfur, nitrogen, and phosphorous. Part or all of the linking group may be a portion of the molecule being linked to the immunosuppressant compound such as, but not limited to, an amino acid residue on a poly(amino acid), for example. In some examples, the linking group comprises an oxime functionality.

The number of heteroatoms in the linking group may be in the range from 0 to about 20, or 1 to about 15, or about 2 to about 10. The linking group may be aliphatic or aromatic. When heteroatoms are present, oxygen is normally present as oxo or oxy, bonded to carbon, sulfur, nitrogen or phosphorous, nitrogen is normally present as nitro, nitroso or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters. One specific embodiment of a linking group comprising heteroatoms is an oxime functionality as mentioned above.

For the most part, when a linking group has a linking functionality (functionality for reaction with a moiety) such as, for example, a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities are linked to amine groups, carboxyl groups, active olefins, alkylating agents, e.g., bromoacetyl. Where an amine and carboxylic acid or its nitrogen derivative or phosphoric acid are linked, amides, amidines and phosphoramides are formed. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed. Various linking groups are well known in the art; see, for example, Cautrecasas, *J. Biol. Chem.* (1970) 245:3059.

Each different antibody is selected for its binding affinity to one or both of two isomeric analytes as described above. Accordingly, a first antibody is prepared and selected by means of an appropriate screening method such that the first antibody exhibits sufficient assay binding affinity for each of the first isomeric analyte and the second isomeric analyte. A second antibody is prepared and selected by means of an appropriate screening method such that the second antibody binds to the first isomeric analyte but exhibits insufficient assay binding affinity for the first isomeric analyte and further exhibits substantially no assay binding affinity for the second isomeric analyte. An antibody with the requisite binding affinity for an analyte as set forth above may be selected by well-known screening methodologies, which include, by way of illustration and not limitation, ELISA, dot blots, Western analysis, and Surface Plasmon Resonance, for example.

General Description of Assays

The following discussion is by way of illustration and not limitation. Any appropriate assay that utilizes an antibody may be employed on portions of the sample in the determinations involved in accordance with the principles described herein. The assays can be performed either without separation (homogeneous) or with separation (heterogeneous) of any of the assay components or products. Heterogeneous assays usually involve one or more separation steps and can be competitive or non-competitive. The assays may be manual or automated.

The sample to be analyzed is one that is suspected of containing an analyte. The samples may be biological samples or non-biological samples. Biological samples may be from a mammalian subject or a non-mammalian subject. Mammalian subjects may be, e.g., humans or other animal species. Biological samples include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum. Non-biological samples including, but not limited to, waste streams, for example, may also be analyzed using compounds in accordance with the principles described herein.

The sample can be prepared in any convenient medium, which may be, for example, an assay medium, which is discussed more fully hereinbelow. In some instances a pretreatment may be applied to the sample such as, for example, to lyse blood cells. In some examples, such pretreatment is performed in a medium that does not interfere subsequently with an assay.

In many embodiments immunoassays involve labeled reagents. Immunoassays that involve labeled reagents include chemiluminescence immunoassays, enzyme immunoassays, fluorescence polarization immunoassays, radioimmunoassays, inhibition assay, induced luminescence assays, and fluorescent oxygen channeling assays, for example.

One general group of immunoassays includes immunoassays using a limited concentration of one of the assay reagents. Another group of immunoassays involves the use of an excess of one or more of the principal reagents. Another group of immunoassays are separation-free homogeneous assays in which labeled reagents modulate the label signal upon binding of one of the antibodies in accordance with the principles described herein to one or both of two isomeric analytes in the sample.

As mentioned above, the assays can be performed either without separation (homogeneous) or with separation (heterogeneous) of any of the assay components or products. Homogeneous immunoassays are exemplified by the EMIT® assay (Siemens Healthcare Diagnostics Inc., Deerfield, Ill.) disclosed in Rubenstein, et al., U.S. Pat. No. 3,817,837, column 3, line 6 to column 6, line 64; the induced luminescence immunoassay ("LOCI® technology") disclosed in U.S. Pat. No. 5,340,716 (Ullman, et al.); immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; enzyme immunoassays such as the enzyme linked immunosorbant assay ("ELISA"). Exemplary of heterogeneous assays are the radioimmunoassay, disclosed in Yalow, et al., J. Clin. Invest. 39:1157 (1960). The above disclosures are all incorporated herein by reference.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), and particle enhanced turbidimetric immunoassay ("PETIA"), etc.; for example.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of a reagent upon the binding of an analyte. Such assays include, for example, optical immunosensor assays, acoustic immunosensor assays, semiconductor immunosensor assays, electrochemical transducer immunosensor assays, potentiometric immunosensor assays, and amperometric electrode assays.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In an example of a competitive heterogeneous assay, a support having an antibody for analyte bound thereto is contacted with a medium containing the sample suspected of containing the analyte and a an analyte analog that comprises a label. Analyte in the sample competes, for binding to the analyte antibody, with the labeled analyte analog. After separating the support and the medium, the label activity of the support or the medium is determined by conventional techniques and is related to the amount of analyte in the sample. In a variation of the above competitive heterogeneous assay, the support comprises an analyte analog, which competes with analyte of the sample for binding to an antibody reagent in accordance with the principles described herein.

In some examples, the sample to be analyzed is subjected to a pretreatment to release analyte from endogenous binding substances such as, for example, plasma or serum proteins that bind the analyte. The release of the analyte from endogenous binding substances may be carried out, for example, by addition of a digestion agent or a releasing agent or a combination of a digestion agent and a releasing agent used sequentially. The digestion agent is one that breaks down the endogenous binding substances so that they can no longer bind the analyte. Such agents include, but are not limited to, proteinase K and proteinase K and protein denaturing agents such as, e.g., detergents (sodium dodecyl sulfate, for example). Releasing agents for releasing the analyte from endogenous binding substances include, by way of illustration and not limitation, acidic denaturing agents such as, for example, salicylic acid, warfarin, sulfonic acids, toluene sulfonic acids, naphthalene sulfonic acid, anilinonaphthalene sulfonic acids (ANS) (including, e.g., 1-anilinonaphthalene-8-sulfonic acid (1,8-ANS) and 8-anilinonapthalene-1-sulfonic acid (8-ANS)), salicylic acids and derivatives of the above.

The conditions such as, for example, duration, temperature, pH and concentration of the releasing agent in the medium for carrying out the digestion or releasing actions are dependent on the nature of the analyte, the nature of the endogenous binding substances, the nature of the sample, and the nature of the releasing agent, for example. In general, the conditions are sufficient to achieve the desired effect or function. In some examples in accordance with the principles described herein, an effective concentration of releasing agent is about 0.01 to about 20 mg/mL, or about 0.01 to about 10 mg/mL, or about 0.01 to about 5 mg/mL, or about 0.1 to about 20 mg/mL, or about 0.1 to about 10 mg/mL, or about 0.1 to about 5 mg/mL, or about 0.1 to about 1 mg/mL. The pretreatment of the sample to release the analyte from endogenous binding substances may be carried out as a separate step prior to conducting an assay or as a first step in an assay. In either case, one or more reagents may be required to stop the action of the digestion agent and/or the releasing agent.

The conditions for conducting an assay on a portion of a sample in accordance with the principles described herein include carrying out the assay in an aqueous buffered medium at a moderate pH, generally that which provides optimum assay sensitivity. The aqueous medium may be solely water or may include from 0.1 to about 40 volume percent of a cosolvent. The pH for the medium will be in the range of about 4 to about 11, or in the range of about 5 to about 10, or in the range of about 6.5 to about 9.5, for example. The pH will usually be a compromise between optimum binding of the binding members of any specific binding pairs, the pH optimum for other reagents of the assay such as members of the signal producing system, and so forth. Various buffers may be used to achieve the desired pH and maintain the pH during the assay. Illustrative buffers include, by way of illustration and not limitation, borate, phosphate, carbonate, TRIS, barbital, PIPES, HEPES, MES, ACES, MOPS, and BICINE, for example. The particular buffer employed is not critical, but in an individual assay one or another buffer may be preferred.

Various ancillary materials may be employed in the assay methods. For example, in addition to buffers the medium may comprise stabilizers for the medium and for the reagents employed. In some embodiments, in addition to these additives, proteins may be included, such as, for example, albumins; organic solvents such as, for example, formamide; quaternary ammonium salts; polyanions such as, for example, dextran sulfate; binding enhancers, for example, polyalkylene glycols; polysaccharides such as, for example, dextran or trehalose. The medium may also comprise agents for preventing the formation of blood clots. Such agents are well known in the art and include, but are not limited to, EDTA, EGTA, citrate, heparin, for example. The medium may also comprise one or more preservatives such as, but not limited to, sodium azide, neomycin sulfate, PROCLIN® 300, Streptomycin, for example. The medium may additionally comprise one or more surfactants. Any of the above materials, if employed, is present in a concentration or amount sufficient to achieve the desired effect or function.

One or more incubation periods may be applied to the medium at one or more intervals including any intervals between additions of various reagents employed in an assay including those mentioned above. The medium is usually incubated at a temperature and for a time sufficient for binding of various components of the reagents and binding of the analyte in the sample to occur. Moderate temperatures are normally employed for carrying out the method and usually constant temperature, preferably, room temperature, during the period of the measurement. In some examples, incubation temperatures range from about 5° to about 99° C., or from about 15° C. to about 70° C., or from about 20° C. to about 45° C., for example. The time period for the incubation, in some examples, is about 0.2 seconds to about 24 hours, or about 1 second to about 6 hours, or about 2 seconds to about 1 hour, or about 1 minute to about 15 minutes, for example. The time period depends on the temperature of the medium and the rate of binding of the various reagents, which is determined by the association rate constant, the concentration, the binding constant and dissociation rate constant.

Many assays discussed herein use a signal producing system, which may have one or more components, at least one component being a label. The signal producing system generates a signal that relates to the presence of an analyte in a sample. The signal producing system includes all of the reagents required to produce a measurable signal. Other components of the signal producing system may be included in a developer solution and can include, but are not limited to, substrates, enhancers, activators, chemiluminescent compounds, cofactors, inhibitors, scavengers, metal ions, and specific binding substances required for binding of signal generating substances, for example. Other components of the signal producing system may be coenzymes, substances that react with enzymic products, other enzymes and catalysts, for example. The signal producing system provides a signal detectable by external means, by use of electromagnetic radiation, desirably by visual examination. Exemplary signal-producing systems are described in U.S. Pat. No. 5,508,178, the relevant disclosure of which is incorporated herein by reference.

The term "label" includes poly(amino acid) labels and non-poly(amino acid) labels. The term "poly(amino acid) label moieties" includes labels that are proteins such as, but not limited to, enzymes, antibodies, peptides, and immunogens, for example. With label proteins such as, for example, enzymes, the molecular weight range will be from about 10,000 to about 600,000, or from about 10,000 to about 300,000 molecular weight. There is usually at least one compound in accordance with the principles described herein (analog group) per about 200,000 molecular weight, or at least about 1 per about 150,000 molecular weight, or at least about 1 per about 100,000 molecular weight, or at least about 1 per about 50,000 molecular weight, for example, of the protein. In the case of enzymes, the number of analog groups is usually from 1 to about 20, about 2 to about 15, about 3 to about 12, or about 6 to about 10.

Enzymes include, by way of illustration and not limitation, redox enzymes such as, for example, dehydrogenases, e.g., glucose-6-phosphate dehydrogenase and lactate dehydrogenase; enzymes that involve the production of hydrogen peroxide and the use of the hydrogen peroxide to oxidize a dye precursor to a dye such as, for example, horseradish peroxidase, lactoperoxidase and microperoxidase; hydrolases such as, for example, alkaline phosphatase and β-galactosidase; luciferases such as, for example firefly luciferase, and bacterial luciferase; transferases; combinations of enzymes such as, but not limited to, saccharide oxidases, e.g., glucose and galactose oxidase, or heterocyclic oxidases, such as uricase and xanthine oxidase, coupled with an enzyme that employs hydrogen peroxide to oxidize a dye precursor, that is, a peroxidase such as horseradish peroxidase, lactoperoxidase or microperoxidase, for example.

The term "non-poly(amino acid) labels" includes those labels that are not proteins. The non-poly(amino acid) label is capable of being detected directly or is detectable through a reaction that produces a detectable signal. The non-poly (amino acid) label can be isotopic or non-isotopic and can be, by way of illustration and not limitation, a radioisotope, a luminescent compound (which includes, but is not limited to fluorescent compounds and chemiluminescent compounds, for example), a polynucleotide coding for a catalyst, a promoter, a dye, a coenzyme, an enzyme substrate, a radioactive group, and an amplifiable polynucleotide sequence, for example.

In some examples one member of the signal producing system is a small organic molecule refers to a molecule of molecular weight of about 200 to about 2,000, or about 200 to about 1,500, or about 200 to about 1,000, or about 200 to about 500. Such small organic molecules include, but are not limited to, biotin, fluorescent molecules (such as fluorescein and rhodamine, for example), chemiluminescent molecules and dinitrophenol, for example. A binding partner for a small organic molecule is a molecule that specifically recognizes and binds to the small molecule. Binding partners for a small molecule are defined by the nature of the small molecule and include, but are not limited to, avidin, streptavidin, antibody for the small organic molecule (which include, but are not limited to, antibody for a fluorescent molecule (such as antibody for fluorescein and antibody for rhodamine, for example), antibody for a chemiluminescent molecule, antibody for dinitrophenol, for example.

In some examples of assays, a support is utilized. The support may be comprised of an organic or inorganic, solid or fluid, water insoluble material and which may be transparent or partially transparent. The support can have any of a number of shapes, such as, but not limited to, a particle (particulate support) including bead, a film, a membrane, a tube, a well, a strip, a rod, a fiber, or a planar surface such as, e.g., a plate or paper, for example. The support may or may not be suspendable in the medium in which it is employed. Examples of suspendable supports are polymeric materials such as latex, lipid bilayers or liposomes, oil droplets, cells and hydrogels, and magnetic particles, for example. Other support compositions include polymers, such as, by way of illustration and not limitation, nitrocellulose, cellulose acetate, poly (vinyl chloride), polyacrylamide, polyacrylate, polyethylene, polypropylene, poly (4 methylbutene), polystyrene, polymethacrylate, poly(ethylene terephthalate), nylon, poly(vinyl butyrate), for example, either used by themselves or in conjunction with other materials. The support may or may not be further labeled with a dye, catalyst or other detectable group, for example.

In some examples, the support may be a particle. The particles have an average diameter of at least about 0.02 microns and not more than about 100 microns. In some examples, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus*, and *E. coli*, viruses, for example. The particles can also be particles comprised of organic and inorganic polymers, liposomes, latex particles, magnetic or non-magnetic particles, phospholipid vesicles, chylomicrons, lipoproteins, and the like. In some examples, the particles are chromium dioxide (chrome) particles or latex particles.

Chemiluminescent particles are particles that have associated therewith a chemiluminescent compound. The phrase "associated therewith" as used herein means that a compound such as, for example, a chemiluminescent compound and a particle may be associated by direct or indirect bonding, adsorption, absorption, incorporation, or solution, for example. Examples of chemiluminescent compounds that may be utilized are those set forth in U.S. Pat. Nos. 5,340,716 and 6,251,581, the relevant disclosures of which are incorporated herein by reference. In some examples in accordance with the principles described herein, the chemiluminescent compound is a photoactivatable substance that undergoes a chemical reaction upon direct or sensitized excitation by light or upon reaction with singlet oxygen to form a metastable reaction product that is capable of decomposition with the simultaneous or subsequent emission of light, usually within the wavelength range of 250 to 1200 nm. The term "photoactivatable" includes "photochemically activatable". In some examples, the chemiluminescent compounds are those that react with singlet oxygen to form dioxetanes or dioxetanones. The latter are usually electron rich olefins. Exemplary of such electron rich olefins are enol ethers, enamines, 9-alkylidene-N-alkylacridans, arylvinylethers, dioxenes, arylimidazoles, 9-alkylidene-xanthanes and lucigenin. Other compounds include luminol and other phthalhydrazides and chemiluminescent compounds that are protected from undergoing a chemiluminescent reaction by virtue of their being protected by a photochemically labile protecting group, such compounds including, for example, firefly luciferin, aquaphorin, and luminol. Examples of such chemiluminescent compounds that may be utilized are those set forth in U.S. Pat. No. 5,709,994, the relevant disclosure of which is incorporated herein by reference.

Sensitizer particles are particles that have associated therewith a sensitizer compound, which includes, but is not limited to, a photosensitizer compound. Examples of sensitizer compounds that may be utilized are those set forth in U.S. Pat. Nos. 5,340,716 and 6,251,581, the relevant disclosures of which are incorporated herein by reference.

A photosensitizer is a sensitizer for generation of singlet oxygen usually by excitation with light. In some examples, the photosensitizer absorbs at a longer wavelength than the chemiluminescent compound and has a lower energy triplet than the chemiluminescent compound. The photosensitizer can be photoactivatable (e.g., dyes and aromatic compounds). The photosensitizer is usually a compound comprised of covalently bonded atoms, usually with multiple conjugated double or triple bonds. The compound should absorb light in the wavelength range of 200-1100 nm, usually 300-1000 nm, preferably 450-950 nm. Typical photosensitizers include, but are not limited to, acetone, benzophenone, 9-thioxanthone, eosin, 9,10-dibromoanthracene, methylene blue, metallo-porphyrins (e.g., hematoporphyrin), phthalocyanines, chlorophylls, rose bengal, buckminsterfullerene, for example, and derivatives of these compounds. Examples of other photosensitizers are enumerated in N. J. Turco, "Molecular Photochemistry", page 132, W. A. Benjamin Inc., N.Y. 1965. The photosensitizer assists photoactivation where activation is by singlet oxygen. Usually, the photosensitizer absorbs light and the thus formed excited photosensitizer activates oxygen to produce singlet oxygen, which reacts with the chemiluminescent compound to give a metastable luminescent intermediate.

Some known assays utilize a signal producing system (sps) that employs first and second sps members. The sps members may be related in that activation of one member of the sps produces a product such as, for example, light or an activated product, which results in activation of another member of the sps.

In an example of such an assay, the sps members comprise a sensitizer such as, for example, a photosensitizer, and a chemiluminescent composition that includes a chemiluminescent compound where activation of the sensitizer results in a product that activates the chemiluminescent composition. The second sps member usually generates a detectable signal that relates to the amount of bound and/or unbound sps member, i.e., the amount of sps member bound or not bound to the analyte being detected. In some examples in accordance with the principles described herein, one of either the sensitizer reagent or the chemiluminescent reagent comprises an antibody reagent in accordance with the principles described herein.

Examples of Methods in Accordance with the Principles Described Herein

As discussed above, methods in accordance with the principles described herein are directed to determining in a sample an amount of a first isomeric analyte and a second isomeric analyte. In the method a first measurement value and a second measurement value are determined. For determination of the first measurement value, a total amount of the first isomeric analyte and the second isomeric analyte is measured by conducting an assay on a first portion of the sample using a first antibody that exhibits sufficient assay binding affinity for each of the first isomeric analyte and the second isomeric analyte. In this example, the first antibody is a monoclonal antibody prepared by one of the procedures described above.

The sample portion can be prepared in any convenient medium that does not interfere with an assay; an aqueous medium generally is employed. The size of the sample portion is dependent on one or more of the nature of the isomeric analytes, the nature of the assay, the nature of the various reagents for conducting the assay, and the nature of the complex comprising the analyte, for example. The size of the sample portion should be essentially the same for both measurements involved in the determination. In some examples, the volume of the sample portion is about 1 µL to about 100 µL, or about 2 µL to about 100 µL, or about 5 µL to about 100 µL, or about 10 µL to about 100 µL, or about 1 µL to about 80 µL, or about 1 µL to about 60 µL, or about 1 µL to about 40 µL, or about 1 µL to about 20 µL, or about 5 µL to about 50 µL, or about 10 µL to about 50 µL, for example.

The assay selected for the determination of the first measurement value is performed on the first sample portion, which may be pretreated as discussed above to release the analyte from endogenous binding substances. An amount of a complex comprising the first antibody for the analyte and the first and second isomeric analytes is measured by measuring a level of signal generated by the complex. Signal observed is related to a total amount of combined first isomeric analyte and second isomeric analyte in the sample.

For determination of the second measurement value, an amount of the second isomeric analyte is measured by conducting the assay on a second portion of the sample using the first antibody and the assay medium further comprises a second antibody that binds to the first isomeric analyte but exhibits insufficient assay binding affinity for the first isomeric analyte and substantially no assay binding affinity for the second isomeric. The second sample portion may be pretreated as discussed above to release the analyte from endogenous binding substances. Alternatively, the sample may be pretreated prior to taking portions to be employed in the methods in accordance with the principles described herein. In this example, the second antibody is a monoclonal antibody prepared by one of the procedures described above. The second antibody is employed in excess relative to the first antibody in the assay medium comprising the second portion of the sample to block binding of the first isomeric analyte to the first antibody. The excess amount is an amount greater than that of the first antibody required to bind a majority of the first isomeric analyte that might be present in a sample. The amount of the second antibody employed depends on the nature of the second antibody, the nature of the first antibody, the nature of the isomeric analytes, the nature of the assay medium, and the nature of the assay, for example. In some examples in accordance with the principles described herein an excess amount of the second antibody is about 5 to about 200 times, or about 5 to about 150 times, or about 5 to about 100 times, or about 5 to about 50 times, or about 10 to about 200 times, or about 10 to about 150 times, or about 10 to about 100 times, or about 10 to about 50 times, or about 20 to about 200 times, or about 20 to about 150 times, or about 20 to about 100 times, or about 20 to about 50 times that of the first antibody, for example. An amount of a complex comprising the first antibody for the analyte and the second isomeric analyte is measured by measuring a level of signal generated by the complex. Signal observed is related to an amount of second isomeric analyte in the sample. The second measurement value is subtracted from the first measurement value to obtain a resulting value and the resulting value is equated to an amount of the first isomeric analyte in the sample.

As discussed more fully above, any suitable assay may be employed. The assay comprises adding reagents for determining the concentration of an analyte in the sample. The reagents include at least the first antibody and the second antibody and, thus, the assay is an immunoassay. The assays conducted on the sample portions may be carried out sequentially or concomitantly in separate reaction vessels or sequentially in the same reaction vessel for each sample portion. The term "complex" refers to a complex wherein antibody for the analyte is bound to analyte in the sample.

As mentioned above, measurements of the isomeric analytes may be carried out on samples that have been treated with a releasing agent. The amount of releasing agent that is added to the sample is that which is sufficient to displace substantially all of the isomeric analytes from the endogenous binding substances. The phrase "displace substantially all of the isomeric analytes that are bound by endogenous binding substances" means that the isomeric analytes are at least 80%, or at least 90%, or at least 95%, or at least 99%, or at least 99.5%, or at least 99.9% or is 100% displaced from endogenous binding substances and available for detection during an assay.

After addition of a releasing agent, the sample is incubated for a period of time under conditions to displace substantially all of the isomeric analytes from endogenous binding substances. The length and conditions of the incubation are dependent on one or more of the nature of the releasing agent, the nature of the analyte, and the suspected concentration of the analyte, for example. In some embodiments incubation temperatures for this step may be about 5° C. to about 99° C., or about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The incubation may be carried out in a medium that, for convenience, may be an assay medium as discussed herein, but need not be.

One particular example in accordance with the principles described herein is directed to a method that employs the following assay reagents on the first and second portions of the sample suspected of containing the analyte: (i) an antibody reagent in accordance with the principles described herein, (ii) a chemiluminescent particle reagent comprising an analyte analog, and (iii) a photosensitizer particle reagent comprising a small molecule-binding moiety or a binding partner for the small molecule.

In the following particular examples, the isomeric analytes are the non-epi and epi forms of vitamin D by way of illustration and not limitation. An induced luminescence immunoassay may be employed. The induced luminescence immunoassay is referred to in U.S. Pat. No. 5,340,716 (Ullman), which disclosure is incorporated herein by reference. In one approach, the assay uses a particle having associated therewith a photosensitizer where a vitamin D analog is bound to the particle (particle-analog reagent). For the assay on the first portion of a sample suspected of containing both the non-epi and the epi forms of vitamin D analyte, the chemiluminescent reagent comprises a first antibody that exhibits sufficient assay binding affinity for each of the non-epi and epi forms of the vitamin D analyte. For the assay on the second portion of a sample, the chemiluminescent reagent comprising the first antibody is employed along with a second antibody that binds to the non-epi form of the vitamin D analyte but exhibits insufficient assay binding affinity for the non-epi form of the vitamin D analyte and substantially no assay binding affinity for the epi form of the vitamin D analyte. In the above example, the first antibody is linked to a small molecule, which is bound to a binding partner for the small molecule on a chemiluminescent particle. This chemiluminescent reagent may be pre-formed or formed in situ. The vitamin D analyte (non-epi and epi forms) competes with the particle-analog reagent for binding to the antibody for vitamin D in accordance with the principles described herein. If the vitamin D analyte is present, the fewer is the number of molecules of particle-analog reagent that come into close proximity with the chemiluminescent reagent. Therefore, there will be a decrease in the assay signal. The photosensitizer generates singlet oxygen and activates the chemiluminescent reagent when the two labels are in close proximity. The activated chemiluminescent reagent subsequently produces light, where a decrease in signal is observed in the presence of the analyte. The amount of light produced is related to the amount of the complex formed, which in turn for the assay on the first sample portion is related to the amount of both the non-epi and epi forms of the vitamin D analyte present in the sample (first measurement value) and for the assay on the second samples portion is related to the amount of the epi form of the vitamin D analyte present in the sample (second measurement value). Subtraction of the second measurement value from the first measurement value gives the amount of the non-epi form of the vitamin D analyte in the sample.

In another particular example of an induced luminescence immunoassay using vitamin D as an example, by way of illustration and not limitation, the assay uses a particle having associated therewith a chemiluminescent compound where a vitamin D analog is bound to the particle (particle-analog reagent). For the first sample portion, a photosensitizer reagent comprises a first antibody that exhibits sufficient assay binding affinity for each of the non-epi and epi forms of the vitamin D analyte, which is linked to a small molecule that is in turn bound to a binding partner for the small molecule on a chemiluminescent particle. For the second sample portion, the photosensitizer reagent and a second antibody are employed. The second antibody binds to the non-epi form of the vitamin D analyte but exhibits insufficient assay binding affinity for the non-epi form of the vitamin D analyte and substantially no assay binding affinity for the epi form of the vitamin D analyte. For the first sample portion, the both the non-epi form and the epi form of the vitamin D analyte compete with the particle-analog reagent for binding to the first antibody for vitamin D. If the vitamin D analyte is present, the fewer is the number of molecules of particle-analog reagent that come into close proximity with the photosensitizer reagent. Therefore, there will be a decrease in the assay signal. For the second sample portion, the epi form of the vitamin D analyte competes with the particle-analog reagent for binding to the first antibody for vitamin D because the non-epi form of the vitamin D analyte is bound by the second antibody. If the epi form of the vitamin D analyte is present, the fewer is the number of molecules of particle-analog reagent that come into close proximity with the photosensitizer reagent. Therefore, there will be a decrease in the assay signal. The photosensitizer generates singlet oxygen and activates the chemiluminescent compound of the particle-analog reagent when the two labels are in close proximity. The activated chemiluminescent compound subsequently produces light, where a decrease in signal is observed in the presence of the analyte. The amount of light produced is related to the amount of the complex formed, which in turn for the assay on the first sample portion is related to the amount of both the non-epi and epi forms of the vitamin D analyte present in the sample (first measurement value) and for the assay on the second samples portion is related to the amount of the epi form of the vitamin D analyte present in the sample (second measurement value). Subtraction of the second measurement value from the first measurement value gives the amount of the non-epi form of the vitamin D analyte in the sample.

In another particular example of an induced luminescence assay using vitamin D by way of illustration and not limitation, a photosensitizer particle is employed that is conjugated to a binding partner for a small molecule such as, for example, avidin or streptavidin (which are binding partners for biotin). An antibody reagent in accordance with the principles described herein that comprises biotin linked to a first antibody that binds to both the non-epimeric and epimeric forms of the vitamin D analyte is employed. A chemiluminescent reagent is employed as part of the detection system. The reaction medium for the first sample portion or the second sample portion, as the case may be, is incubated to allow the avidin or streptavidin of the photosensitizer particles to bind to the biotin of the antibody reagent by virtue of the binding between avidin and biotin and to also allow the specific binding between the first antibody of the antibody reagent in accordance with the principles described herein, which is now attached to the photosensitizer particles, to bind to the analyte of the sample and to the analyte that is part of the chemiluminescent reagent. Then, the medium is irradiated with light to excite the photosensitizer, which is capable in its excited state of activating oxygen to a singlet state. Because less of the chemiluminescent reagent is now in close proximity to the photosensitizer because of the presence of the analyte, there is less activation of the chemiluminescent reagent by the singlet oxygen and less luminescence. The medium is then examined for the presence and/or the amount of luminescence or light emitted, the presence thereof being related to the presence and/or amount of the analyte where a decrease in signal is observed in the presence of the analyte. The amount of light produced is related to the amount of the complex formed, which in turn for the assay on the first sample portion is related to the amount of both the non-epi and epi forms of the vitamin D analyte present in the sample (first measurement value) and for the assay on the second samples portion is related to the amount of the epi form of the vitamin D analyte present in the sample (second measurement value). Subtraction of the second measurement value from the first measurement value gives the amount of the non-epi form of the vitamin D analyte in the sample.

Another example of an assay format for detection of vitamin D, by way of illustration and not limitation, in a sample is the ACMIA assay format. For the ACMIA assay format, chrome particles, which are coated with vitamin D or a vitamin D analog (chrome particle reagent), are employed as a first component. A second component is an antibody reagent that comprises an antibody for vitamin D in accordance with the principles described herein. In the antibody reagent, the antibody is linked by means of a linking group to a reporter enzyme (for example, β-galactosidase) to form an antibody-enzyme conjugate. The antibody reagent is added to a reaction vessel in an excess amount, i.e., an amount greater than that required to bind all of the vitamin D analyte that might be present in a sample. A first portion of a sample, which is previously subjected to treatment with a releasing agent, is treated with a first antibody reagent as described above, which comprises an antibody that exhibits sufficient assay binding affinity for each of the non-epi and epi forms of the vitamin D analyte; the antibody binds to vitamin D in the sample. The antibody-enzyme conjugate is mixed with sample in the medium to allow the vitamin D analyte to bind to the antibody. Next, the chrome particle reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the amount of both the non-epi and epi forms of the vitamin D in the sample. A second portion of a sample, which is previously subjected to treatment with a releasing agent, is treated with the first antibody reagent and a second antibody as described above, which comprises a second antibody, which binds to the non-epi form of the vitamin D analyte but exhibits insufficient assay binding affinity for the non-epi form of the vitamin D analyte and substantially no assay binding affinity for the epi form of the vitamin D. The antibody-enzyme conjugate is mixed with sample in the medium to allow the vitamin D analyte to bind to the antibody. Next, the chrome particle reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the amount of both the non-epi and epi forms of the vitamin D in the sample.

Another example of an assay for isomeric forms of vitamin D (by way of illustration and not limitation) in a sample is an acridinium ester label immunoassay using paramagnetic particles as a solid phase (ADVIA immunoassay). The detection system employed for this example of a vitamin D assay includes a small molecule-labeled vitamin D (capture moiety) as the small molecule conjugate or capture conjugate, binding partner for the small molecule-coated paramagnetic latex particles as a solid phase (SP), and an acridinium ester labeled antibody for vitamin D (detection antibody) in accordance with the principles described herein. The small molecule may be, for example, biotin or fluorescein and the respective binding partner may be streptavidin or antibody for fluorescein. The vitamin D may be linked to the small molecule directly or through a linking group such as, for example, a protein, e.g., bovine serum albumin (BSA). Vitamin D in a patient sample competes with vitamin D of the capture moiety for binding to the acridinium ester labeled detection anti-vitamin D antibody. The sample suspected of containing vitamin D is subjected to a pretreatment with 1,8-ANS. The assay may be carried out on first and second sample portions using respective antibodies in accordance with the principles described herein and a CENTAUR®, CENTAUR® XP or CENTAUR® CP apparatus (Siemens Healthcare Diagnostics Inc., Newark Del.) in accordance with the manufacturer's directions supplied therewith.

Another example of an assay for an analyte in accordance with the principles described herein is an acridinium ester label immunoassay using paramagnetic particles as a solid phase (ADVIA immunoassay). The detection system employed for this example of an assay for isomeric analytes includes an antibody reagents in accordance with the principles described herein, in which a small molecule is linked to the antibody for the analyte (capture antibody) as the capture conjugate, paramagnetic latex particles as a solid phase (SP) coated with a binding partner for the small molecule of the antibody reagent, and an acridinium ester labeled analyte analog (detection hapten). The acridinium ester label may be directly bound to the analyte to form the detection hapten or a linking group may be employed including, for example, a protein such as, e.g., BSA. The analyte of a sample competes with the acridinium ester labeled detection hapten for binding with anti-analyte antibody. The sample suspected of containing the analyte may be subjected to a pretreatment with one or more of a releasing agent and a digestion agent. The assay may be carried out on the first and second sample portions using a CENTAUR®, CENTAUR® XP or CENTAUR® apparatus (Siemens Healthcare Diagnostics Inc., Newark Del.) in accordance with the manufacturer's directions supplied therewith. In variations of the above acridinium ester assays, the small molecule may be, for example, biotin or fluorescein and the binding partners for the small molecule may be, for example, avidin or streptavidin or antibody for fluorescein, respectively.

The concentration of the isomeric analytes in a sample that may be assayed generally varies from about $10^{-5}$ to about $10^{-17}$ M, or from about $10^{-6}$ to about $10^{-14}$ M, for example. Considerations such as whether the assay is qualitative, semi-quantitative or quantitative (relative to the amount of the analyte present in the sample), the particular detection technique and the expected concentration of the analyte normally determine the concentrations of the various reagents.

The concentrations of the various reagents in the assay medium will generally be determined by the concentration range of interest of the analyte, the nature of the assay, and the like. However, the final concentration of each of the reagents is normally determined empirically to optimize the sensitivity of the assay over the range of interest. That is, a variation in concentration of analyte that is of significance should provide an accurately measurable signal difference. Considerations such as the nature of the signal producing system and the nature of the analytes normally determine the concentrations of the various reagents.

As mentioned above, the sample and reagents are provided in combination in the medium. While the order of addition to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, each of the reagents, or groups of reagents, can be combined sequentially. In some embodiments, an incubation step may be involved subsequent to each addition as discussed above. In heterogeneous assays, washing steps may also be employed after one or more incubation steps.

Some examples in accordance with the principles described herein are directed to methods of determining one or both of the presence and the amount of one or both of two isomeric forms of vitamin D in a sample suspected of containing vitamin D and may be referred to herein as "assays for vitamin D." As used herein in reference to assays, the term "vitamin D" refers to one or more of the non-epi and epi forms of one or more of 25-hydroxycholecalciferol (also referred to as calcidiol, calcifediol, 25-hydroxycholecalciferol, or 25-hydroxyvitamin D (abbreviated 25(OH)D); calcidiol; 1,25-dihydroxyvitamin $D_3$ (calcitriol; 1,25(OH)$_2$D$_3$); 1,25-dihydroxy vitamin $D_4$; 1,25-dihydroxy vitamin $D_5$; and 1,25-dihydroxy vitamin $D_6$; including metabolites of all of the above.

Examination Step

In one step of an assay method, the medium is examined for the presence of a complex comprising one or more isomeric forms of the analyte and antibody for an analyte in accordance with the principles described herein. The presence and/or amount of one or both of the complexes indicates the presence and/or amount of one or more of the isomeric forms of the analyte in the sample.

The phrase "measuring the amount of analyte" refers to the quantitative, semiquantitative and qualitative determination of one or more of the isomeric forms of an analyte. Methods that are quantitative, semiquantitative and qualitative, as well as all other methods for determining the analyte, are considered to be methods of measuring the amount of the analyte. For example, a method, which merely detects the presence or absence of the analyte in a sample suspected of containing the analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal is related to the presence and/or amount of one or more of the isomeric forms of an analyte in the sample. The particular mode of detection depends on the nature of the signal producing system. As discussed above, there are numerous methods by which a label of a signal producing signal can produce a signal detectable by external means. Activation of a signal producing system depends on the nature of the signal producing system members.

Temperatures during measurements generally range from about 10° C. to about 70° C. or from about 20° C. to about 45° C., or about 20° C. to about 25° C., for example. In one approach standard curves are formed using known concentrations of vitamin D analyte. Calibrators and other controls may also be used.

Luminescence or light produced from any label can be measured visually, photographically, actinometrically, spectrophotometrically, such as by using a photomultiplier or a photodiode, or by any other convenient means to determine the amount thereof, which is related to the amount of analyte in the medium. The examination for presence and/or amount of the signal also includes the detection of the signal, which is generally merely a step in which the signal is read. The signal is normally read using an instrument, the nature of which depends on the nature of the signal. The instrument may be, but is not limited to, a spectrophotometer, fluorometer, absorption spectrometer, luminometer, and chemiluminometer, for example.

Kits Comprising Reagents for Conducting Assays

Kits for conducting assays on portions of a sample suspected of containing isomeric forms of an analyte may be prepared. The kits comprise antibody reagents for assays to be carried out on respective portions of the sample. Accordingly, one antibody reagent comprises an antibody that exhibits sufficient assay binding affinity for each of a first isomeric analyte and a second isomeric analyte. A second antibody is included that binds to the first isomeric analyte but exhibits insufficient assay binding affinity for the first isomeric analyte and substantially no assay binding affinity for the second isomeric analyte. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional specific binding pair members, signal producing system members, and ancillary reagents, for example.

The relative amounts of the various reagents in the kits can be varied widely to provide for concentrations of the reagents that substantially optimize the reactions that need to occur during the present methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay using a compound reagent in accordance with the principles described herein. The kit can further include a written description of a method utilizing reagents that include a compound reagent in accordance with the principles described herein.

The designation "first" and "second" as used herein is completely arbitrary and is not meant to suggest any order or ranking among moieties referred to or any order of addition of moieties in the present methods.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The following discussion is directed to specific examples in accordance with the principles described herein by way of illustration and not limitation; the specific examples are not intended to limit the scope of the present disclosure and the appended claims. Numerous modifications and alternative compositions, methods, and systems may be devised without departing from the spirit and scope of the present disclosure.

EXAMPLES

Unless otherwise indicated, materials in the experiments below may be purchased from the Sigma-Aldrich Chemical Corporation (St. Louis Mo.) or Fluka Chemical Corporation (Milwaukee Wis.). Parts and percentages disclosed herein are by weight to volume unless otherwise indicated.

DEFINITIONS mg=milligram
g=gram(s)
ng=nanogram(s)
mL=milliliter(s)
μL=microliter(s)
μmol=micromolar
° C.=degrees Centigrade
min=minute(s)
sec=second(s)
hr=hour(s)
w/v=weight to volume
v/v=volume to volume
TLC=thin layer chromatography
HPLC=high performance liquid chromatography
EDTA=ethylenediaminetetraacetate
PEG=polyethylene glycol
EtOAc=ethyl acetate
DMF=dimethylformamide
DMSO=dimethylsulfoxide
MeOP=1-methoxy-2-propanol
MES=2-(N-morpholino)ethanesulfonic acid
DI=distilled
UPA=Ultra Particle Analyzer
LOCI=luminescent oxygen channeling immunoassay
Ab=antibody Preparation of Biotinylated First Antibody that Exhibits Sufficient Assay Binding Affinity for Both Non-Epi Vitamin D and Epi-Vitamin D A solution (0.8 mL at 2.63 mg/mL) of vitamin D antibody 5H10 (sheep monoclonal from Bioventix, Farnham, Surrey, UK) in 10 mM $PO_4$, 300 mM NaCl, pH 7.0 was mixed with 43.2 μL of an aqueous solution (2.0 mg/mL) of NHS-dPEG®4-biotin (Quanta Biodesign Ltd., Powell Ohio, part number 10200). The amount of biotinylation reagent added represents a 10-fold molar challenge of the biotinylating agent with the antibody. The reaction mixture was incubated at room temperature for 3 hr and then the reaction was quenched by addition of 80 μL of 0.5 M TRIS. The reaction mixture was subjected to buffer exchange with 10 mM PO$_4$, 300 mM NaCl, pH 7.0 in an AMICON® (YM10) device until absorption at 260 nm of the effluent was <0.03. The antibody solution (1.04 mL at 2.1 mg/mL protein) was mixed with 10 μL of PROCLIN® 300 and 10 μL of an aqueous solution of neomycin sulfate (10 mg/mL) filtered using a 0.2 μm ACRODISC® syringe filter (Pall Corporation) and was stored at 2-8° C.

Preparation of EPRM-EDA Beads

EPRM beads (2000 mg, 20.0 mL) are added to a 40-mL vial. The EPRM beads are prepared by a procedure similar to that described in U.S. Pat. No. 7,179,660 and the chemiluminescent compound is 2-(4-(N,N, di-tetradecyl)-anilino-3-phenyl thioxene with europium chelate. EDA (800 mg, 890 μL) is combined with 10 mL MES pH 6 buffer (the "Buffer") and about 4.2 mL 6N HCl. The pH of the mixture is, or is adjusted to be, about 6.9. The EDA solution is added to the EPRM beads with vortexing and the mixture is rocked at room temperature for 15 minutes. Sodium cyanoborohydride (400 mg) is combined in a 15 mL vial with 10 mL DI water and the combination is added to the bead mixture from above. The mixture is shaken at 37° C. for 18-20 hours. The beads are transferred to six 40 mL centrifuge tubes. MES buffer is added to bring the volume to 35 mL and the mixture is centrifuged at 19,000 rpm for 30 min. The supernatant is decanted and the beads are re-suspended in 2 mL of the Buffer with a stir-rod and additional Buffer is added to 35 mL. The mixture is sonicated at 18 Watts power for 30 sec, using ice to keep the mixture cold. The wash/sonication step is performed 4 times to remove all activation chemical. After the last MES Buffer centrifugation, 2 mL of the Buffer containing 5% MeOP and 0.1% Tween® 20 (the "second Buffer") is added to the tubes for the re-suspension step. Additional second buffer is added to 35 mL before sonication. The bead suspension is centrifuged at 19,000 rpm for 30 min. The supernatant is discarded. The final sonication used 12 mL of the second Buffer in each tube to give a 25 mg/mL dilution. Particle size is 277 nm as determined on a UPA instrument.

The EPRM chemibead is prepared in a manner similar to the method described in U.S. Pat. No. 6,153,442 and U.S. Patent Application Publication No. 20050118727A, the relevant disclosures of which are incorporated herein by reference. The EPRM chemibead comprises an aminodextran inner layer and a dextran aldehyde outer layer having free aldehyde functionalities. See, for example, U.S. Pat. Nos. 5,929,049, 7,179,660 and 7,172,906, the relevant disclosures of which are incorporated herein by reference. The reaction is carried out at a temperature of about 0 to about 40° C. for a period of about 16 to about 64 hours at a pH of about 5.5 to about 7.0, or about 6, in a buffered aqueous medium employing a suitable buffer such as, for example, MES. The reaction is quenched by addition of a suitable quenching agent such as, for example, carboxymethoxyamine hemihydrochloride (CMO), and subsequent washing of the particles.

Aldehyde groups on the outer dextran aldehyde layer are reacted with ethylene diamine under reductive amination conditions to form reagent EPRM-EDA having pendant moieties comprising an ethylene chain and a terminal amine group. The reductive amination conditions include the use of a reducing agent such as, for example, a metal hydride. The reaction is carried out in an aqueous medium at a temperature during the reaction of about 20° C. to about 100° C. for a period of about 1 hour to about 48 hours.

Synthesis of 25-OH Vitamin D$_3$ 3-Carbamate (25-OH Vitamin D$_2$ 3-Carbamate)

A mixture of 22 mg (55 μmol) 25-OH VD$_3$ purchased from ChemReagents.com, Sugarland Tex., 100 mg (420 μmol) disuccinimidyl carbonate (DSC), 100 μL triethylamine in 1 mL anhydrous acetonitrile in a 5-ml flask (covered with foil) was stirred at room temperature for 18 hr under nitrogen to prepare activated 25-OH VD$_3$. TLC (EtOAc: Hexane=2:1) showed no starting material left. A suspension was prepared by adding 150 mg of carboxymethoxyamine hemihydrochloride (CMO), 0.3 ml triethylamine and 1 ml DMF to a 10 ml flask. A solution containing activated 25-OH VD$_3$ was added dropwise to the CMO suspension with stirring, which was continued for another 18 hr. Vacuum was applied to remove the solvents as much as possible (the heating bath temperature should not be over 50° C.). EtOAc (25 ml) was added to the residue, which was washed three times with 2 ml brine. The organic phase was dried with anhydrous Na$_2$SO$_4$ and was filtered; solvent was removed using rotavap. Crude product (42 mg) was obtained after drying and was purified by HPLC. Pure product (24 mg) was obtained after being dried under high vacuum. The product was dissolved into 1.2 ml anhydrous DMSO. Aliquots were transferred into vials, which were kept at −70° C.

Coupling of EPRM-EDA and 25-OH Vitamin D$_3$ 3-Carbamate to Give Chemibead Reagent 25-OH Vitamin D$_3$ 3-Carbamate (10 μL of aliquot in DMSO prepared as described above) (0.2 mg) was added to a 2-mL vial. EDAC (6.8 mg) and SNHS (9.4 mg) plus 2.27 mL dry DMSO (3 mg/mL) were added to a 5-mL vial. The EDAC/SNHS solution (190 μL) was combined with the contents of the 2-mL vial from above (1 mg/mL) to prepare activated 25-OH vitamin D$_3$ 3-carbamate. The mixture was allowed to rotate at room temperature for 18 hr. A 0.4 mL aliquot of a 16% GAFAC® surfactant solution (GAF Corporation, Wayne N.J.) (0.15%) was diluted to 1.6% with 3.6 mL DI water.

Vitamin D$_3$ (8.5 mg) and 850 μL DMSO (10 mg/mL) were combined. To a 10-mL round bottom flask (labeled 3323-064B) equipped with a stir-bar was added 2.0 mL (200MG) EPRM-EDA followed by 400 μL (4 mg) of the Vitamin D$_3$ solution from above. The mixture stirred overnight at room temperature.

To a 10-mL round bottom flask equipped with a stir-bar was added 2.0 mL (200 mg) EPRM-EDA (prepared as described above) followed by 260 μL 1.6% GAFAC® surfactant solution (0.15%) with moderate stirring. To a small test tube was added 504 μL anhydrous DMSO followed by 60 μL (0.06 mg) activated Vitamin D$_3$-3-carbamate prepared as described above; and the mixture was added to the EPRM-EDA bead mixture. The total DMSO content of the bead suspension was 20%. The reaction vessel was allowed to stir overnight at room temperature. Then, the beads were washed by means of diafiltration.

Each bead lot was taken up to 20 mL working volume with 10% MeOP/1% GAFAC®/MES pH6 buffer. The mixture was diafiltered with 5 volumes of the buffer and then sonicated with a probe sonicator at 18-21 Watts using ice to keep the mixture cold. The diafiltration/sonication continued through 50 volumes with effluent samples being taken at 35, 40, 45 and 50 volumes. The buffer was changed to LOCI Hapten Wash Buffer (50 mM HEPES, 300 mM NaCl, 1 mM EDTA, 0.01% neomycin sulfate, 0.1% TRITON® 405×and 0.15% PROCLIN® 300, pH 7.2) with 10 volumes being used. The mixture was reduced to about 7 mL and a UPA performed. Particle sizes were 3323-064A=289 nm and 3323-064B=298 nm. Percent solids were determined and the bead lot was brought up to 10 mg/mL with LOCI Hapten Wash Buffer pH7.2. Yield was 160.4 mg.

Assay for Non-Epi-Vitamin D and Epi-Vitamin D

Assays were carried out on a DIMENSION® VISTA® analyzer (Siemens Healthcare Diagnostics Inc., Deerfield, Ill.) following the protocol for a LOCI assay and using calibrator solutions containing varying amounts of non-epi-25-hydroxyvitamin $D_3$ and/or 3-epi-25-hydroxyvitamin $D_3$. In this example, the assay uses, as a chemiluminescent reagent, the chemibead reagent prepared as described above. Sample portions are reacted with either (i) the first biotinylated antibody reagent (first sample portion) prepared as described above or (ii) the first biotinylated antibody and a second antibody (second sample portion) and then with the chemibead reagent. For the second sample portion, the second antibody is a solution (0.8 mL at 2.63 mg/mL) of vitamin D antibody 10H9 (mouse monoclonal found in CENTAUR® vitamin D assay, Siemens Healthcare Diagnostics Inc., Newark Del.); the second antibody was present in excess amount (75 µg/mL or 100 times that of the 5H10 antibody). The chemibeads bind to the fraction of the monoclonal antibody binding sites that is not occupied by analyte from the sample. Subsequently, streptavidin coupled sensitizer beads are added to the reaction mixture. This leads to the formation of chemibead/sensibead pairs whose concentration is inversely related to a concentration of either both forms of the vitamin D (first sample portion) or the epi form of vitamin D (second sample portion). Upon illumination at 680 nm, the sensitizer beads generate singlet oxygen which diffuses into the chemibeads which are paired with sensibeads, reacts with the olefinic dye and triggers a chemiluminescent signal at approximately 612 nm which is inversely related to the analyte concentration.

The streptavidin-sensitizer bead ("sensibead(s)") is prepared using a method analogous to that described in U.S. Pat. Nos. 6,153,442, 7,022,529, 7,229,842 and U.S. Patent Application Publication No. 20050118727A. The photosensitizer was bis-(trihexyl)-silicon-t-butyl-phthalocyanine. The concentration of sensibead reagent was 200 µg/mL in HEPES buffer, pH 8.0 containing 150 mM NaCl. The EPRM-EDA-25-OH Vitamin $D_3$ particle reagent prepared as described above was employed as the "chemibead reagent" at a concentration of 200 µg/mL in HEPES buffer, pH 7.2, containing 150 mM NaCl and 0.1% detergent.

For a respective sample portion, at time t=zero sec, 20 µL biotinylated antibody reagent and 20 µL water were added to a reaction vessel. Sample, 12 µL, was added 21.6 seconds later, followed by 8 µL water. At t=414.0 seconds, 40 µL chemibead reagent was added followed by 20 mL of water. Sensibead reagent was then dispensed at 457.2 seconds. Measurements were taken 601.2 seconds after initiation of the reaction sequence. A first measurement value representing an amount of both the epi and non-epi forms of vitamin D and a second measurement value representing an amount of only the epi form of vitamin D were obtained.

Figure 3:
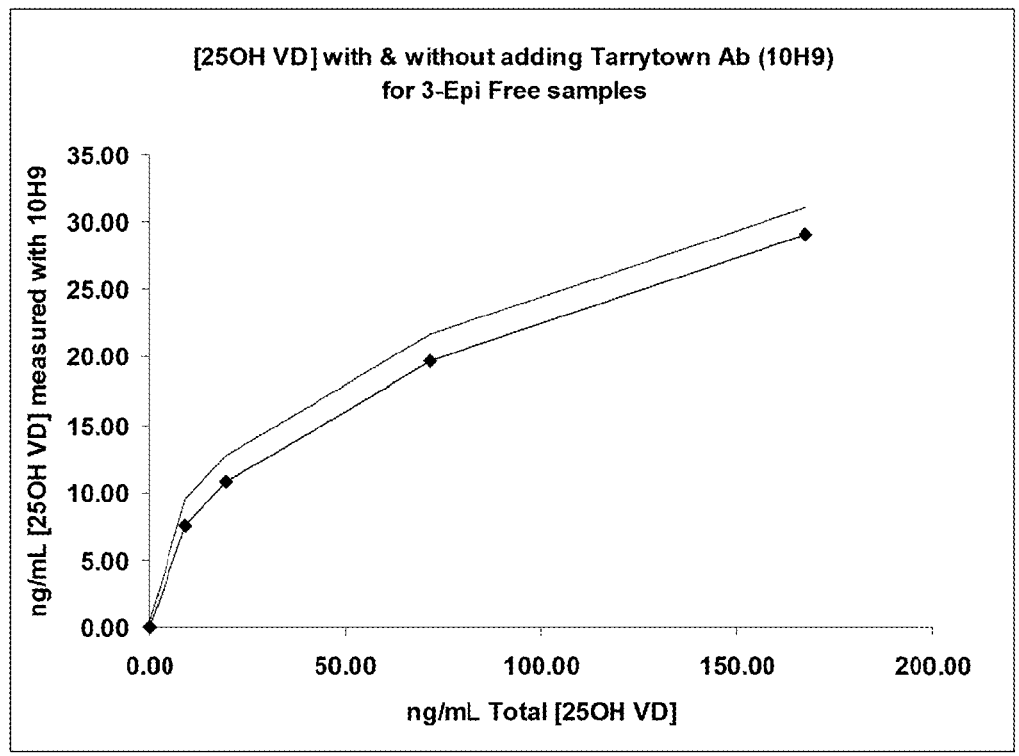
FIG. 3 is a graph depicting vitamin D measurements of 3-epi-25-hydroxyvitamin $D_3$ with and without the addition of a second antibody in accordance with examples in accordance with the principles described herein.

Using the above assay format, assays were carried out on serum samples that were spiked with varying amounts of non-epi-25-hydroxyvitamin $D_3$ (non-epi-VD) but not with 3-epi-25-hydroxyvitamin $D_3$ (3-epi-VD). This set of assays was performed to calibrate the instrument and the samples that contained or did not contain 10H9 second antibody. The results are summarized in Table 1 below and are plotted in a graph depicted in FIG. 3.

TABLE 1

| 10H9 Ab absent Non-epi-VD (ng/mL) | 10H9 Ab present Non-epi-VD (ng/mL) |
|---|---|
| 0.0 | 0.0 |
| 9.2 | 7.5 |
| 19.6 | 10.8 |
| 71.6 | 19.7 |
| 167 | 29.1 |

The results show that the assay is still detecting some non-epi-VD even with an excess amount of the 10H9 second antibody present. Therefore, results obtained in other assays employing the 10H9 second antibody on this instrument system will have to be adjusted to account for the results of this calibration.

Figure 2:
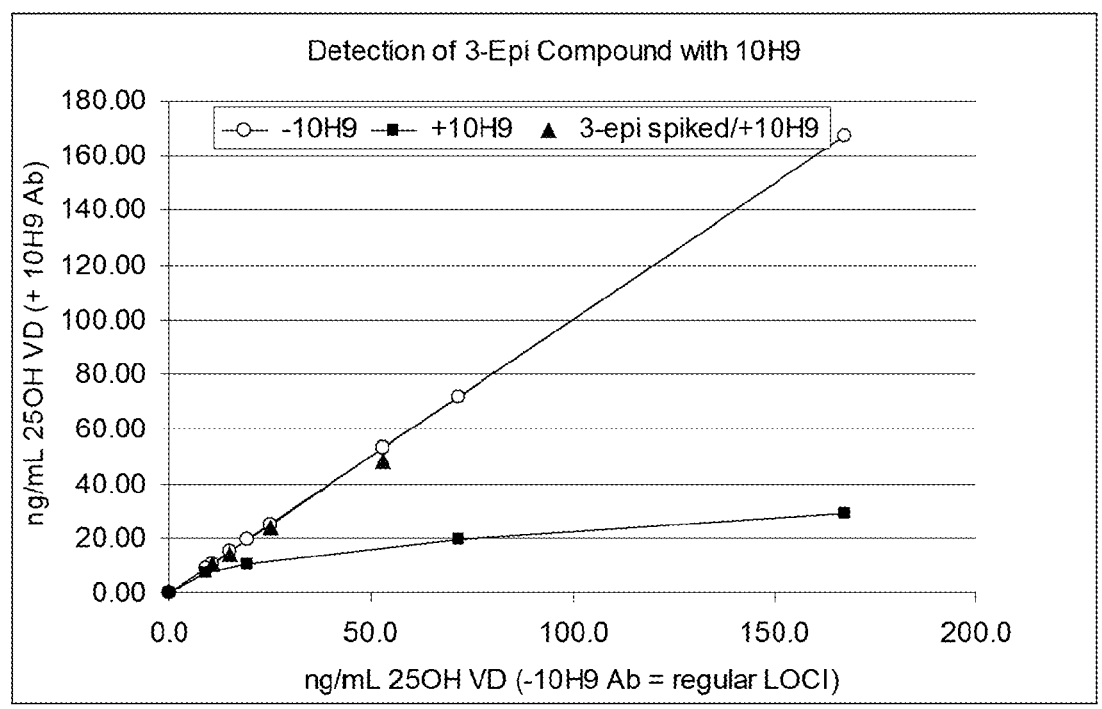
FIG. 2 is a graph depicting vitamin D measurements of 3-epi-25-hydroxyvitamin $D_3$ with and without the addition of a second antibody in accordance with examples in accordance with the principles described herein.

Using the above assay format, assays were carried out on serum samples that were spiked with varying amounts of non-epi-VD and with 3-epi-VD. The assays were carried out both with (+10H9) and without (−10H9) the 10H9 second antibody. The "Predicted 1" and "Predicted 2" values are obtained with reference to the graphs in FIGS. 2 and 3. Values are ng/mL; Diff=difference between +10H9 value and Predicted 1 value. "Amount spiked" is the amount of 3-epi-VD that was spiked into the samples. The results are summarized in Table 2 below.

TABLE 2

| −10H9 | +10H9 | Predicted 1 | Diff | 3-epi-VD present | Predicted 2 | Amount spiked |
|---|---|---|---|---|---|---|
| 53 | 48.5 | 18 | 30.6 | Yes | 170 | 167 |
| 25.2 | 24.1 | 12 | 12.1 | Yes | 67 | 70 |
| 15.3 | 14.5 | 9 | 5.7 | Yes | 32 | 30 |
| 10.8 | 10.6 | 7 | 7 | Yes | 20 | 10 |
| 9.2 | 7.5 | 6 | 1.2 | No | 0 | 0 |
| 19.6 | 10.8 | 10 | 0.5 | No | 0 | 0 |
| 71.6 | 19.7 | 21 | −0.9 | No | 0 | 0 |

Using the above data in Table 2, a corrected amount of 3-epi-VD is calculated as follows; the predicted amount of 3-epimer is listed in the second to the last column. Explanations for each column of Table 2 above are as follows:

Column 1: −10H9 is ng/mL 25(OH)D measured in the absence of 10H9 Ab. This represents the total amount of 25(OH)D ng/mL ($D_2$+$D_3$+3epi×cross-reactivity)

Column 2: +10H9 is ng/mL 25(OH)D measured in the presence of 10H9 Ab. This represents suppressed total 25(OH)D ng/mL (partial D2+partial D3+3epi×cross-reactivity)

Column 3: Predicted 1 is the amount of ng/mL 25(OH)D in the presence of 10H9 if there were no 3-epimer present in sample (partial $D_2$+partial $D_3$)

Column 4: Diff is column 2 minus column 3=3epi×cross-reactivity

Column 5: Predicted 2 is column 4 divided by cross-reactivity or (3epi×cross-reactivity)/cross-reactivity=3epi ng/mL)

Column 6: Amount spiked is how much 3-epimer is spiked in sample. This column should be compared to column 5 to show how close the results are in column 5 and column 6.

The results are summarized in Table 3. Corrected means 25(OH)D ng/mL calculated after the measured 3-epimer ng/mL is subtracted from the total ng/mL 25(OH)D measured in the absence of 10H9 Ab. CXR means 3-epimer cross-reactivity of the 2 reaction vessel assay after 3-epimer interference is removed. This is not the same as the cross-reactivity referred to above. The cross-reactivity in Table 2 is the cross-reactivity of 5H10 Ab with the 3-epimer. The cross-reactivity in Table 3 is the cross-reactivity of the assay after the concentration of 3-epimer is subtracted from the final ng/mL 25(OH)D concentration.

TABLE 3

| −10H9 | +10H9 | Amount Spiked | Diff | 3-epi-VD present | Corrected | 3-epi-VD CXR |
|---|---|---|---|---|---|---|
| 53 | 48.5 | 167 | 30.6 | Yes | 14 | 3% |
| 25.2 | 24.1 | 70 | 12.1 | Yes | 10 | 2% |
| 15.3 | 14.5 | 30 | 5.7 | Yes | 10 | 3% |
| 10.8 | 10.6 | 10 | 7 | Yes | 9 | 2% |
| 9.2 | 7.5 | 0 | 1.2 | No | 0 | 0 |
| 19.6 | 10.8 | 0 | 0.5 | No | 0 | 0 |
| 71.6 | 19.7 | 0 | −0.9 | No | 0 | 0 |

In Table 3, the columns 1, 2, 3, 4 and 5 correspond to columns 1, 2, 7, 4 and 5 in Table 2, respectively. Column 6 is corrected, which is ng/mL 25(OH)D without 3-epimer. Basically, ng/mL 25(OH)D values for calibrators L2-L5 was plotted against the differences in ng/mL between 25(OH)D values in the presence and absence of 10H9 antibody. The coefficients generated from this plot were used to predict non-3-epimer 25(OH)D values by the differences. This results because the difference is the suppressed signal that represents non-3-epimer signal since 10H9 antibody only binds to non-epimers.

All publications and patent applications cited in this specification are herein incorporated by reference as if each individual publication or patent application were specifically and individually indicated to be incorporated by reference.

It should be understood that the above-described examples are merely illustrative of some of the many specific examples that represent the principles described herein. Clearly, those skilled in the art can readily devise numerous other arrangements without departing from the scope as defined by the following claims.

Unless otherwise indicated, materials in the experiments below may be purchased from the Sigma-Aldrich Chemical Corporation (St. Louis Mo.) or Fluka Chemical Corporation (Milwaukee Wis.). Parts and percentages disclosed herein are by weight to volume unless otherwise indicated.

What is claimed is:

1. A method of determining in a sample an amount of non-epi-25-hydroxy vitamin $D_3$ and 3-epi-25-hydroxy vitamin $D_3$, the method comprising:
   (a) conducting an assay on a first portion of the sample using an assay protocol wherein assay reagents utilized in the assay protocol of this step (a) comprise vitamin $D_3$ conjugated to a label and a first antibody that is vitamin D monoclonal antibody 5H10 to form a first complex comprising the first antibody and non-epi-25-hydroxy vitamin $D_3$ and a second complex comprising the first antibody and 3-epi-25-hydroxy vitamin $D_3$, wherein the first complex and the second complex include vitamin $D_3$ conjugated to a label, wherein an amount of signal from the first complex and the second complex is related to a total amount of non-epi-25-hydroxy vitamin $D_3$ and 3-epi-25-hydroxy vitamin $D_3$ in the sample to obtain a first measurement value;
   (b) conducting the assay on a second portion of the sample using the same assay protocol as in step (a) wherein assay reagents utilized in the assay protocol of this step (b) comprise the vitamin $D_3$ conjugated to a label and the first antibody, wherein a second antibody that is vitamin D monoclonal antibody 10H9 is employed in an amount of about 5 to about 200 times the amount of the first antibody, wherein the second antibody binds the non-epi-25-hydroxy vitamin $D_3$ such that the non-epi-25-hydroxy vitamin $D_3$ does not bind to the first antibody, wherein a complex is formed comprising the first antibody and the epi-25-hydroxy vitamin $D_3$, wherein the complex includes the vitamin $D_3$ conjugated to a label, wherein an amount of signal from the complex is related to an amount of the 3-epi-25-hydroxy vitamin $D_3$ in the sample to obtain a second measurement value, thereby determining the amount of 3-epi-25-hydroxy vitamin $D_3$ in the sample; and
   (c) determining an amount of the non-epi-25-hydroxy vitamin $D_3$ in the sample by subtracting the second measurement value from the first measurement value.

2. The method according to claim 1, wherein the assay protocol is a competitive homogeneous assay protocol.

3. The method according to claim 1, wherein the assay protocol employs reagents that comprise a particle.

4. The method according to claim 1, wherein the assay protocol employs reagents that comprise a photosensitizer particle reagent and a chemiluminescent particle.

\* \* \* \* \*